United States Patent
Tsuang et al.

(10) Patent No.: US 8,876,841 B2
(45) Date of Patent: Nov. 4, 2014

(54) SPINAL DISC ANULUS REPAIR METHOD AND APPARATUS

(75) Inventors: Yang-Hwei Tsuang, Taipei (TW); Huang-Chien Liang, Hsinchu (TW); Chun-Hung Chen, Hsinchu County (TW); Chun-Jen Liao, Taipei (TW); Chang-Jung Chiang, Taichung (TW); Chih-Hong Yang, Taichung (TW)

(73) Assignee: Industrial Technology Research Institute, Hsinchu (TW)

( * ) Notice: Subject to any disclaimer, the term of this patent is extended or adjusted under 35 U.S.C. 154(b) by 1105 days.

(21) Appl. No.: 12/505,722

(22) Filed: Jul. 20, 2009

(65) Prior Publication Data

US 2011/0015654 A1   Jan. 20, 2011

(51) Int. Cl.
*A61B 17/04* (2006.01)
*A61B 17/06* (2006.01)
*A61B 17/29* (2006.01)

(52) U.S. Cl.
CPC ... *A61B 17/0469* (2013.01); *A61B 2017/06042* (2013.01); *A61B 17/0482* (2013.01); *A61B 2017/2943* (2013.01); *A61B 2017/0472* (2013.01)
USPC ............ 606/144; 606/139; 606/145; 606/148

(58) Field of Classification Search
USPC ......... 606/139, 144, 145, 146, 148, 222, 223; 623/17.16
See application file for complete search history.

(56) References Cited

U.S. PATENT DOCUMENTS

| | | |
|---|---|---|
| 6,482,235 B1 | 11/2002 | Lambrecht et al. |
| 6,508,839 B1 | 1/2003 | Lambrecht et al. |
| 6,592,625 B2 | 7/2003 | Cauthen |
| 6,984,247 B2 | 1/2006 | Cauthen |
| 6,997,956 B2 | 2/2006 | Cauthen |
| 7,004,970 B2 | 2/2006 | Cauthen, III et al. |
| 7,033,395 B2 | 4/2006 | Cauthen |
| 7,052,516 B2 | 5/2006 | Cauthen, III et al. |
| 7,094,258 B2 | 8/2006 | Lambrecht et al. |
| 7,189,235 B2 | 3/2007 | Cauthen |
| 7,220,281 B2 | 5/2007 | Lambrecht et al. |
| 7,258,700 B2 | 8/2007 | Lambrecht et al. |
| 2002/0116010 A1* | 8/2002 | Chung et al. ............... 606/139 |
| 2002/0116011 A1* | 8/2002 | Chee Chung et al. ........ 606/145 |
| 2002/0198542 A1* | 12/2002 | Yamamoto et al. ........... 606/144 |
| 2003/0045891 A1* | 3/2003 | Yamamoto et al. ........... 606/144 |

(Continued)

OTHER PUBLICATIONS

Davis, et al."Nucleus Arthroplasty Technology in Spinal Care". Volume II: Biomechanics & Development, pp. 1-56. (2007).

(Continued)

*Primary Examiner* — Mark Mashack
*Assistant Examiner* — Jing Ou
(74) *Attorney, Agent, or Firm* — Cesari and McKenna, LLP

(57) ABSTRACT

An apparatus for anulus fibrosus repair includes a shaft, a pair of curved suturing needles mounted in parallel on the shaft, and a rotational driving mechanism connected to the shaft, which is configured to rotate the shaft and the pair of needles about a rotation axis of the shaft. Each needle includes a substantially semi-annular body having a proximal end, a distal end, an inner periphery, and an outer periphery, and an arm extending radially inward from the proximal end, in which a concavity is formed in the body proximate to the distal end extending in a direction away from it. Also disclosed is a suturing technique associated with use of the repair apparatus.

5 Claims, 8 Drawing Sheets

(56) References Cited

U.S. PATENT DOCUMENTS

| | | | | |
|---|---|---|---|---|
| 2004/0236353 | A1* | 11/2004 | Bain et al. | 606/139 |
| 2005/0149067 | A1* | 7/2005 | Takemoto et al. | 606/144 |
| 2005/0228407 | A1* | 10/2005 | Nobles et al. | 606/144 |
| 2005/0234479 | A1* | 10/2005 | Hatch et al. | 606/144 |
| 2006/0282088 | A1* | 12/2006 | Ryan | 606/144 |
| 2006/0282093 | A1* | 12/2006 | Shelton et al. | 606/144 |
| 2007/0276414 | A1* | 11/2007 | Nobles | 606/148 |

OTHER PUBLICATIONS

O'Halloran, et al. "Tissue-Engineering Approach to Regenerating the Intervertebral Disc." Tissue Engineering, vol. 12, Num. 8, pp. 1927-1954 (2007).

Ahlgren et al. "Effect of Anular Repair on the Healing Strength of the Intervertebral Disc—A Sheep Model". SPINE vol. 25, Num 17, pp. 2165-2170 (2000).

* cited by examiner

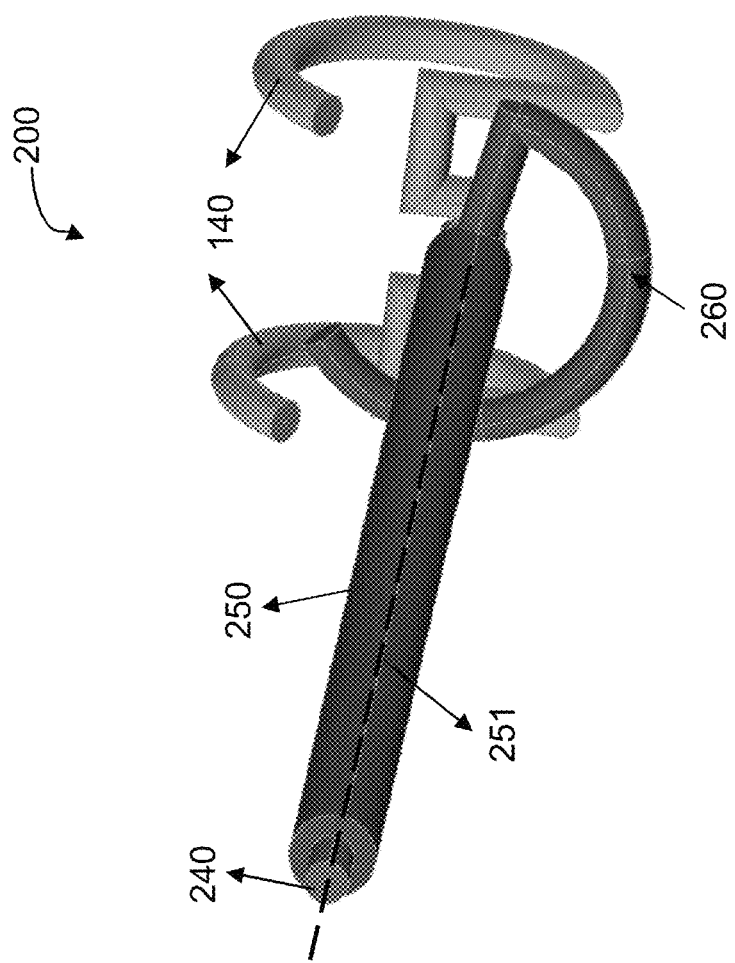

SPINAL DISC ANULUS REPAIR METHOD AND APPARATUS

BACKGROUND

This specification relates to methods of repairing spinal disc anulus fibrosus and apparatuses for practicing the methods.

The intervertebral disc, lying between adjacent vertebrae in the spine, is a vital structure of highly specialized and organized deformable cartilage, without which the spine would be incapable of supporting loads or maintaining flexibility. In a healthy intervertebral disc, the nucleus pulposus (NP) in the central portion is capable of sustaining and transmitting loads while the outer anulus fibrosus (AF) surrounding the nucleus provides both resistances to stresses and movements of the spine.

Defects of the AF (e.g., circumferential delamination and radial fissures) can result in extrusion of otherwise contained NP tissue, known as spinal disc herniation. Particularly in the posterior region, disc protrusions or fragments of NP can cause pain as they displace the nerve root exiting from the dural sac. Among various methods of treating the herniated intervertebral discs, discectomy (i.e., nucleus removal) is generally considered as a standard of care today. It has been reported that surgically repairing defects in the AF in conjunction with and at the conclusion of discectomy may enhance both the technical and clinical outcomes after these procedures. See, e.g., Yasargil, *Adv. Neurosurg.* (1977), 4:81, and Cauthen, *Spinal Arthoplasty: A New Era in Spine Care* (2005), 157-177.

In the past, surgeons have considered and tried suturing the anulus closed using standard sutures, needles, and microsurgical techniques. In a posterior approach, exposure limitations during microdiscectomy make standard suturing difficult to perform. There is a need for developing new suturing techniques and apparatuses to repair defects in the anulus fibrosus following microdiscectomy.

SUMMARY

Accordingly, one general aspect of this invention relates to an apparatus for AF repair, particularly for suturing the anulus closed post a microdiscectomy. The apparatus includes a shaft, a rotational driving mechanism connected to the shaft, and a pair of curved suturing needles mounted in parallel on the shaft. Each needle includes a substantially semi-annular body having a proximal end, a distal end, a tip at the distal end an inner periphery, an outer periphery, and an arm extending radially inward from the proximal end, in which a concavity, having a permanent opening that faces the distal end, is formed in the body proximate to the distal end. The concavity extends from the permanent opening only in a direction away from the tip. The pair of needles are mounted in parallel on the shaft such that the shaft extends through an end of the arm of each needle opposed to the proximal end and in a direction transverse to a plane formed by the body and the arm. A longitudinal axis of the shaft corresponds to a rotation axis of the shaft. The pair of needles each have a co-center of the inner and outer peripheries, both of which are on the rotation axis. The rotation driving mechanism is configured to rotate the shaft and the pair of needles about the rotation axis.

Embodiments of this apparatus may include one or more of the following features.

The rotational driving mechanism may be a device for transmitting a first rotary motion to a second rotary motion. More specifically, the driving mechanism may include a gear system and a bar, in which the gear system has a first gear coaxially connected to the shaft and a second gear that is perpendicularly engaged with the first gear and coaxially connected to the bar. Alternatively, the rotational driving mechanism may be a device for converting a reciprocating linear motion to rotation. More specifically, the rotational driving mechanism includes a pole and a crank connecting the pole with the shaft, the crank being configured to convert a reciprocating linear motion of the pole to rotation of the shaft about the rotation axis. The apparatus can also include a tube member configured to support and partially house the bar. The tube member has a first open end, a second open end opposed to the first end, and a longitudinal axis substantially parallel to a longitudinal axis of the bar. The apparatus can further include a loop drawing device which has a pair of hooks mounted in parallel on an end of a second bar substantially perpendicular to the shaft. Each of the pair of hooks is aligned opposed to each of the pair of needles for seizing a loop of a suture passing through the concavity of each needle, and the second bar is supported and partially housed by the tube member. The apparatus can also include a third needle mounted on an end of a second pole that is coaxially mounted on the pole. The third needle is configured for seizing a loop of a suture passing through the concavity of each needle. The second pole is configured to slide along a longitudinal axis of the pole.

Another general aspect of the invention relates to a curved suturing needle including a substantially semi-annular body having a proximal end, a distal end, an inner periphery, and an outer periphery, and an arm extending radially inward from the proximal end. A concavity is formed in the body proximate to the distal end, extending in a direction away from the distal end.

Embodiments of this needle may include one or more of the following features.

The inner and outer peripheries can be concentric on a reference point, and an end of the arm opposed to the proximal end can have a center superposed on the reference point. The end of the arm can be configured to be mounted on a rotational axis that is perpendicular to a plane formed by the body and the arm. The concavity can be formed in the inner periphery of the body or at the distal end of the body. The body can have a radius r and an arc length greater than $1\pi r$ and less than $1.75\pi r$. The radius r can be from 1 mm to 50 mm (e.g., 1 mm to 10 mm).

Also within the scope of the invention is a method of repairing an AF defect. The method includes loading a suture to an anulus repair apparatus, which has a pair of curved suturing needles each having a substantially semi-annular body in which a concavity for holding the suture is formed, so that the suture passes through the concavity of each needle, the suture having by a first end and a second end; placing the apparatus approximate to the defect; driving the pair of needles to rotate so that the needles carry the suture into the anulus fibrosus near a first edge of the defect, and out of the anulus fibrosus near a second edge of the defect opposed to the first edge, so as to form a pair of loops of the suture; passing the first end of the suture through the pair of loops of the suture; and tying the first end to the second end of the suture whereby the first edge and the second edge of the defect are approximated.

Embodiments of this method may include one or more of the following features.

The repair apparatus used for this method can be the apparatus just described above. The method can further include, before the driving step, placing a patch in the anulus fibrosus and across the defect. The patch can be formed of an autograft, allograft, or xenograft.

The details of one or more embodiments are set forth in the accompanying description below. Other aspects, features, and advantages will be apparent from the following drawing, detailed description of embodiments, and also from the appending claims.

BRIEF DESCRIPTION OF DRAWINGS

FIGS. 5A and 5B are perspective views of a prototype of a second embodiment of an anulus repair apparatus.

DETAILED DESCRIPTION

Figure 1A:
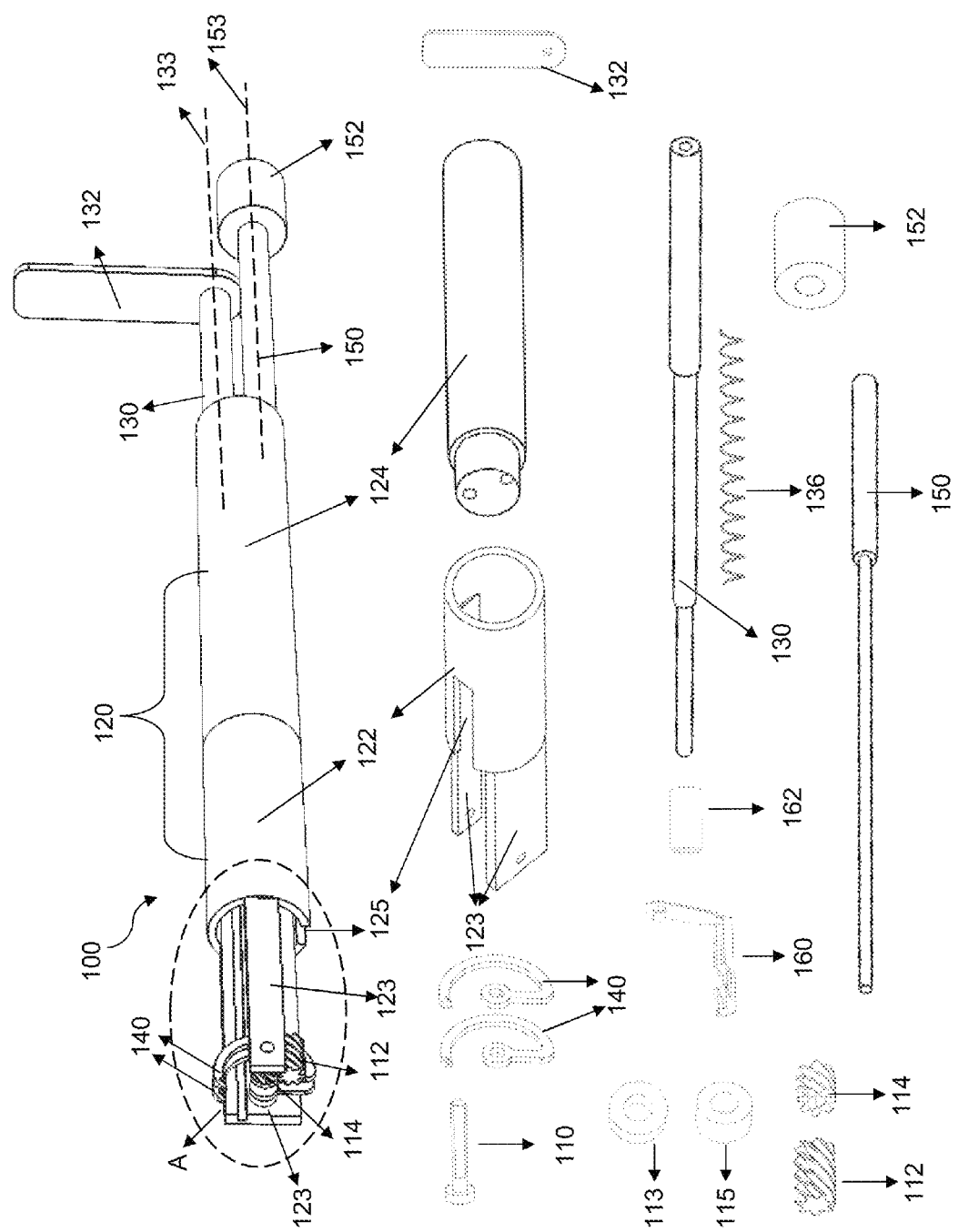
FIG. 1A is a perspective view of a prototype of a first embodiment of an anulus repair apparatus and certain components in disassembled form.
Figure 1B:
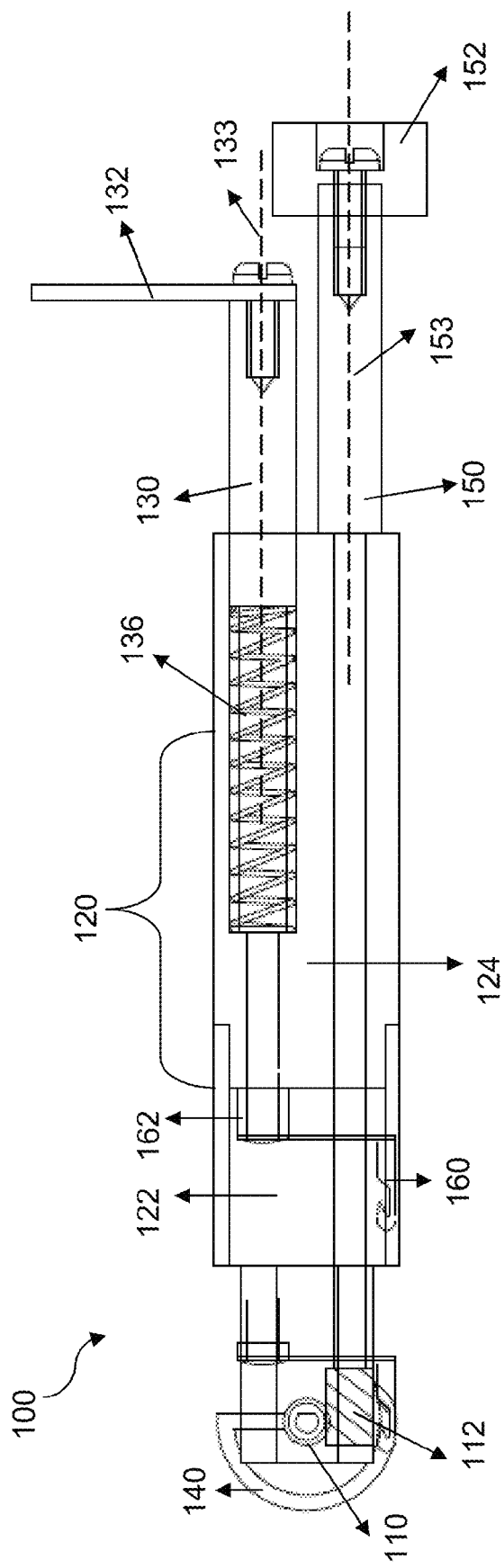
FIG. 1B is a cross-sectional view of the anulus repair apparatus of FIG. 1A.
Figure 1C:
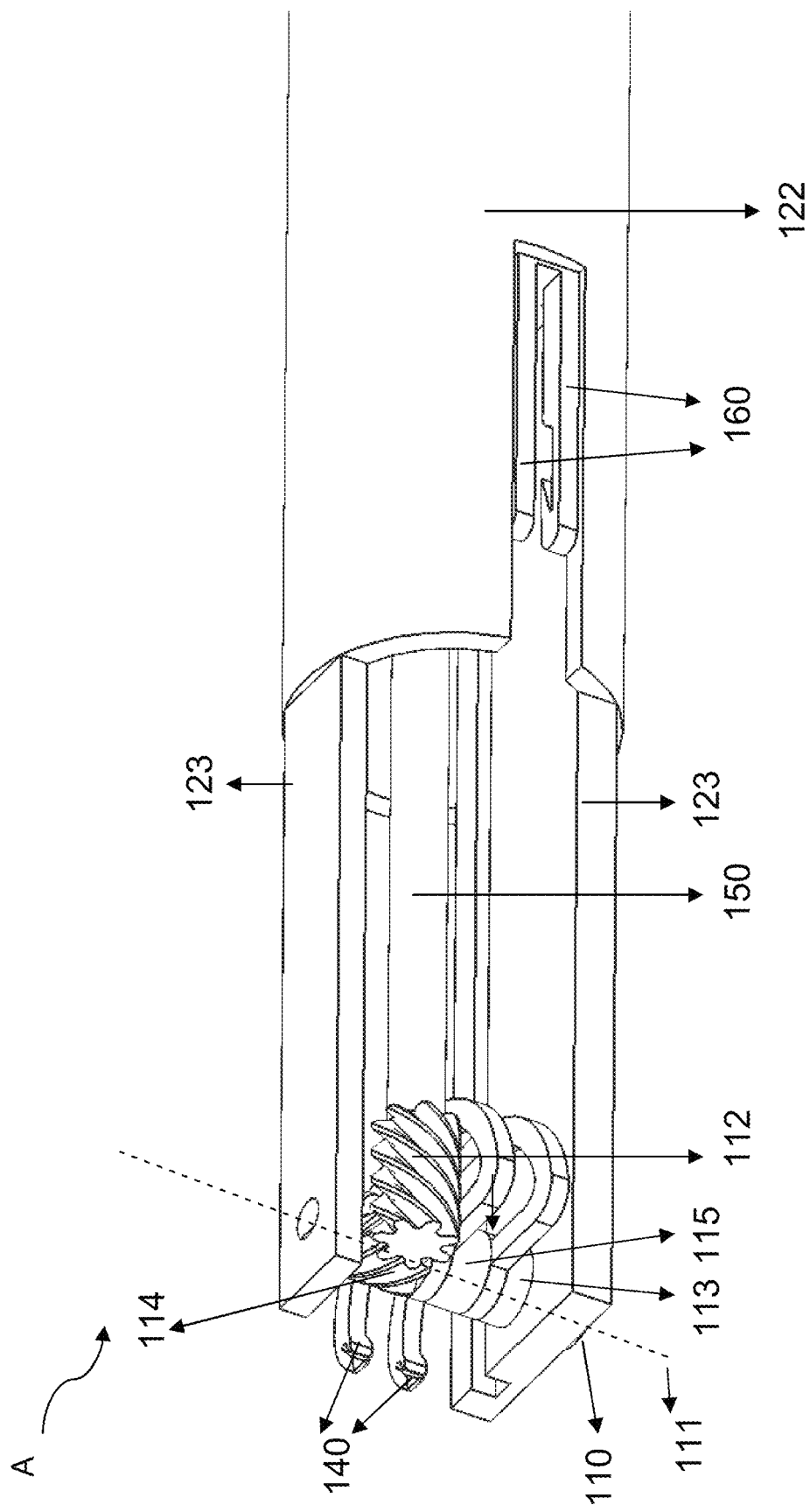
FIG. 1C is an enlarged perspective view of the circled area "A" in FIG. 1A.

FIGS. 1A-1C illustrate a prototype of one embodiment of the anulus repair apparatus of this invention.

As shown in FIGS. 1A and 1B, apparatus 100 includes a tube member 120 partially housing two bars 130 and 150 and a pair of curved needles 140 mounted adjacent one end of the tube member. Tube member 120 is assembled with a fore sleeve 122 and a main sleeve 124. The main sleeve 124 is a solid cylinder having two parallel bores along the longitudinal direction of the sleeve, which are configured to support bars 130 and 150 and allow them to move along or rotate about their rotational axes 133 and 153 respectively. The fore sleeve 122 has one large bore along the longitudinal direction of the sleeve and a pair of parallel plates 123 extending from one end of the fore sleeve. The plates support the shaft on which the needles 140 are mounted. Groove 125 on the wall of the fore sleeve is configured to guide the longitudinal movement of bar 130. As more clearly displayed in FIG. 1C, the pair of needles 140 are mounted in parallel on shaft 110 supported by bearings (not shown) in two plates 123 mounted in parallel on fore sleeve 122. Shaft 110 has a rotation axis 111. When it rotates about axis 111, needles 140 also rotate about axis 111 to carry a suture (not shown) to a predetermined location where a pair of hooks 160, aligned opposed to each of the pair of needles 140, can seize the suture and draw it away from the needles. Needles 140 are separated from each other by washer 115 and separated from the plate 123 by washer 113. As shown in FIG. 1B, both axes 133 and 153 are substantially perpendicular to rotation axis 111 (shown as a dot for it is vertical to the plane of the figure).

Figure 2:
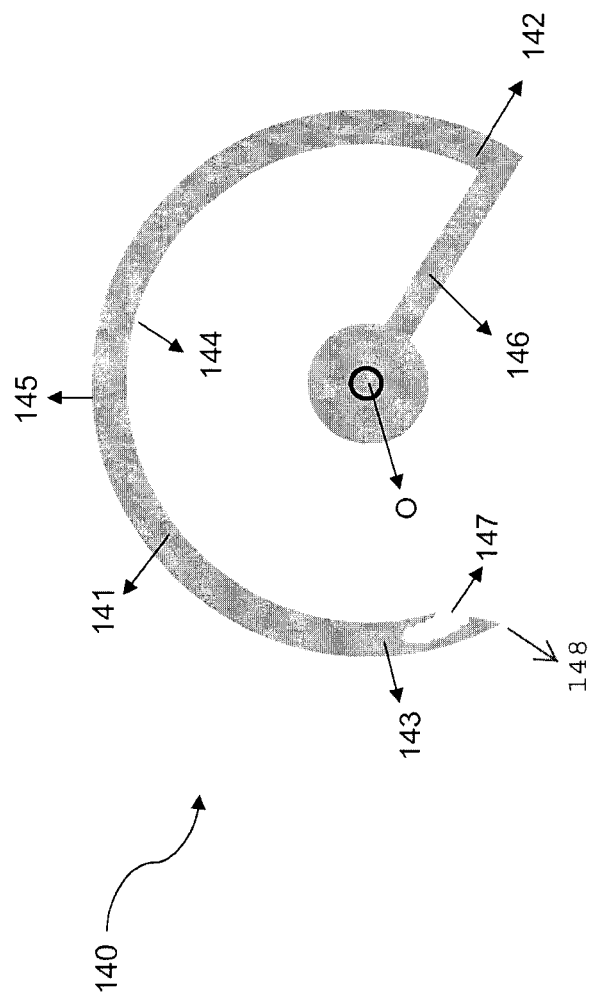
FIG. 2 is a schematic of a curved needle in the apparatus of FIG. 1A.

Referring to FIG. 2, curved needle 140 has a substantially semi-annular body 141 defined by a proximal end 142, a distal end 143, an inner periphery 144, an outer periphery 145, and a tip 148. Body 141 has a radius r and an arc length greater than πr. A concavity 147 for carrying a suture is formed in the inner periphery of the body proximate to the distal end. The concavity extends in a direction away from the distal end so as to allow ready release of the suture upon withdrawal of the needle. The curved needle also has an arm 146 extending radially inward from proximal end 142. The arm is configured to facilitate mounting the needle body on shaft 110. The inner and outer peripheries are concentric on point "O" on the arm, where shaft 110 and arm 146 are engaged.

Figure 3:
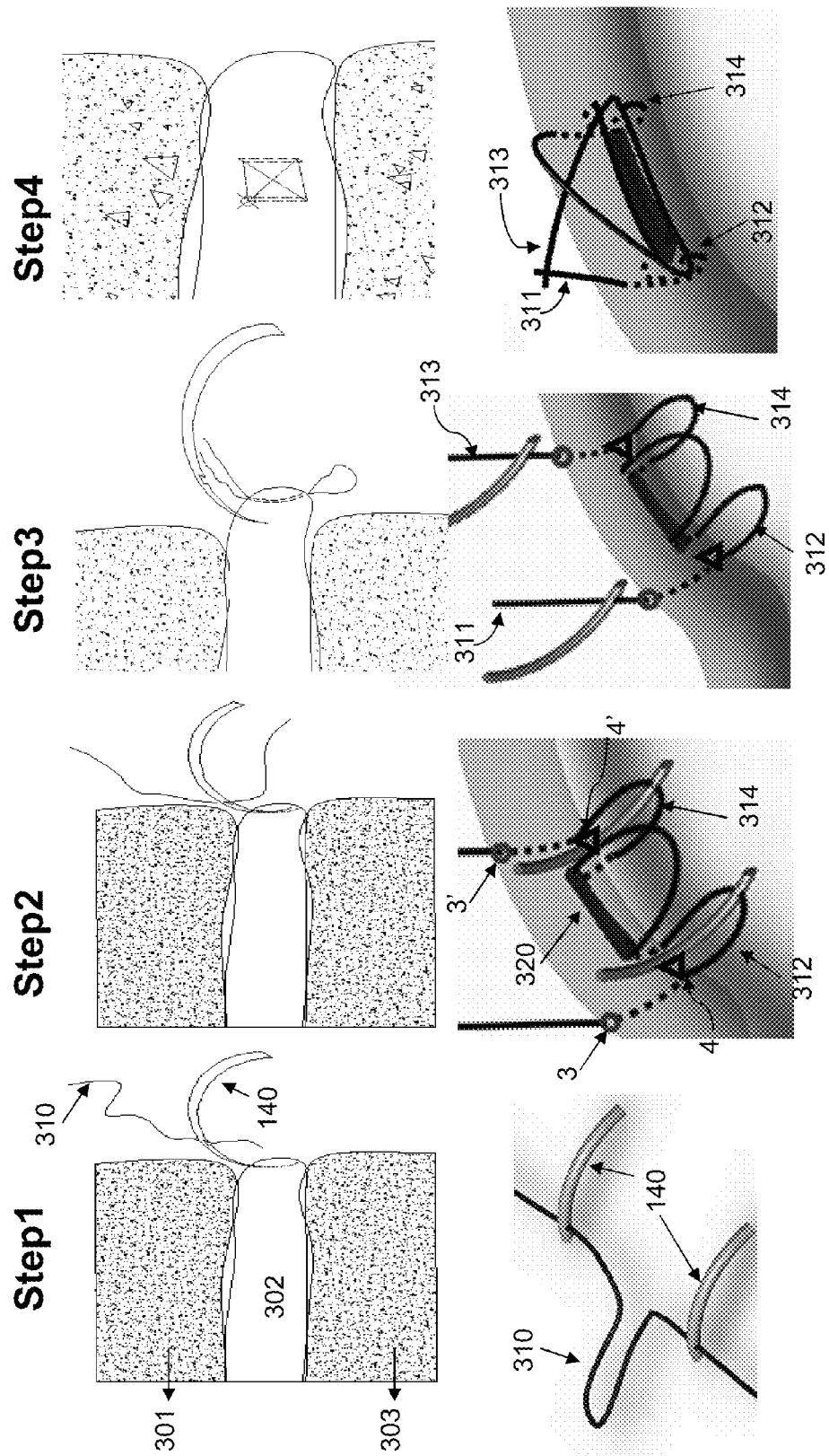
FIG. 3 is a schematic of performing modified purse-string suturing in four steps.

The specific configuration of the pair of needles described above facilitates repairing an AF defect with the modified purse-string suturing ("MPSS") technique of this invention. Referring to FIG. 3, four steps to perform MPSS are illustrated in both sectional/elevated views (i.e., the four top panels) and perspective views (i.e., the four bottom panels). In step 1, the pair of curved needle 140, loaded with a surgical suture 310 through the concavity of each needle, are brought proximate to an defect 320 in a disc anulus 302 between vertebrae 301 and 303. In step 2, the pair of needles synchronously carry suture 310 into the AF near an edge of the defect (at circles 3 and 3' as shown in the prospective view) and out of the AF near the opposing edge of the defect (at triangles 4 and 4' as shown in the prospective view). As a result, a pair of loops of the suture, 312 and 314, are formed at triangles 4 and 4', respectively. In step 3, the pair of needles are withdrawn from the AF, leaving the suture 310 maintained in AF. As shown in FIG. 2, the concavity of each of the needles extends in a manner to facilitate release of the suture when withdrawing the needles from the AF. Loops 312 and 314 may be drawn further away from defect 320 or needles 140 by a loop drawing device (e.g., the pair of hooks 160 mounted on bar 130 as shown in FIG. 1A) to facilitate step 4. The loops can be drawn simultaneously with, before, or after withdrawal of the needles. In step 4, an end 313 of the suture is carried by, e.g., a needle, to pass through loop 312 then loop 314, and lastly tied to end 311 of the suture to approximate the two edges of the defect, thereby close up the defect. The suture pattern thus formed is shown in the elevated view of step 4. The closure of the AF defect enhances the natural healing and subsequent reconstruction by the natural tissue (e.g., fibroblasts) crossing the now surgically narrowed gap in the anulus. Preferably, the surgical suture 310 is biodegradable, but permanent non-biodegradable may be utilized.

The method can be augmented by the placement of a patch of human muscle fascia or any other autograft, allograft or xenograft in the anulus and across defect 320. The patch acts as a bridge in and across the defect, providing a platform for traverse of fibroblasts or other normal cells of repair existing in and around the various layers of the disc anulus 302, prior to closure of the defect. Materials of the patch can be selected from annular, cartilage tissue, ligament soft tissue, collagen, gelatin, PLLA, or PLGA.

In embodiments, the movements of needles 140 are driven by the rotation of shaft 110. The shaft, on the other hand, is driven to rotate by bar 150 drives via a device for transmitting a rotary motion to another rotary motion such as a gear system. Referring back to FIGS. 1A and 1B, rotation of shaft 110 is achieved by turning knob 152 secured on an end of bar 150 to rotate the bar about axis 153, which in turn rotates a pair of helical gears in a crossed configuration, i.e., gear 112 (connected to the other end of bar 150) and gear 114 (connected to shaft 110). Alternatively, bar 150 can drive shaft 110 to rotate via a device for converting a linear motion to a rotary motion such as a crankshaft-piston system. An example of such device is described in more detail below.

As described above. Bar 130 and the pair of hooks 160 are applied as a loop drawing device. Hooks 160, mounted in parallel on an end of bar 130 via fastener 162, is brought adjacent needles 140 by driving the bar toward the needles along axis 133. In one embodiment, a spring 136 (as shown in FIGS. 1A and 1B) is coaxially mounted on bar 130, to allow withdrawal of hooks 160 and thus to draw the loops away from needles 140, upon releasing the driving force applied to plate 132 perpendicularly mounted on the bar.

When using the apparatus of this invention to repair a defect in AF such as a microdiscectomy wound, a guiding kit can be used to precisely dispose the apparatus proximate to the defect. As an example, the guiding kit includes a catheter, a cylinder, and a tube. The cylinder has an outer diameter that matches or slightly greater than that of tube member 120 and an inner diameter that matches the outer diameter of the catheter. The tube has an inner diameter that matches the outer diameter of the cylinder. The catheter first guides the cylinder to the proximity of a defect, which in turn guides the tube to the same location. Eventually, the tube guides the apparatus to be placed proximate to the defect.

Figure 4:
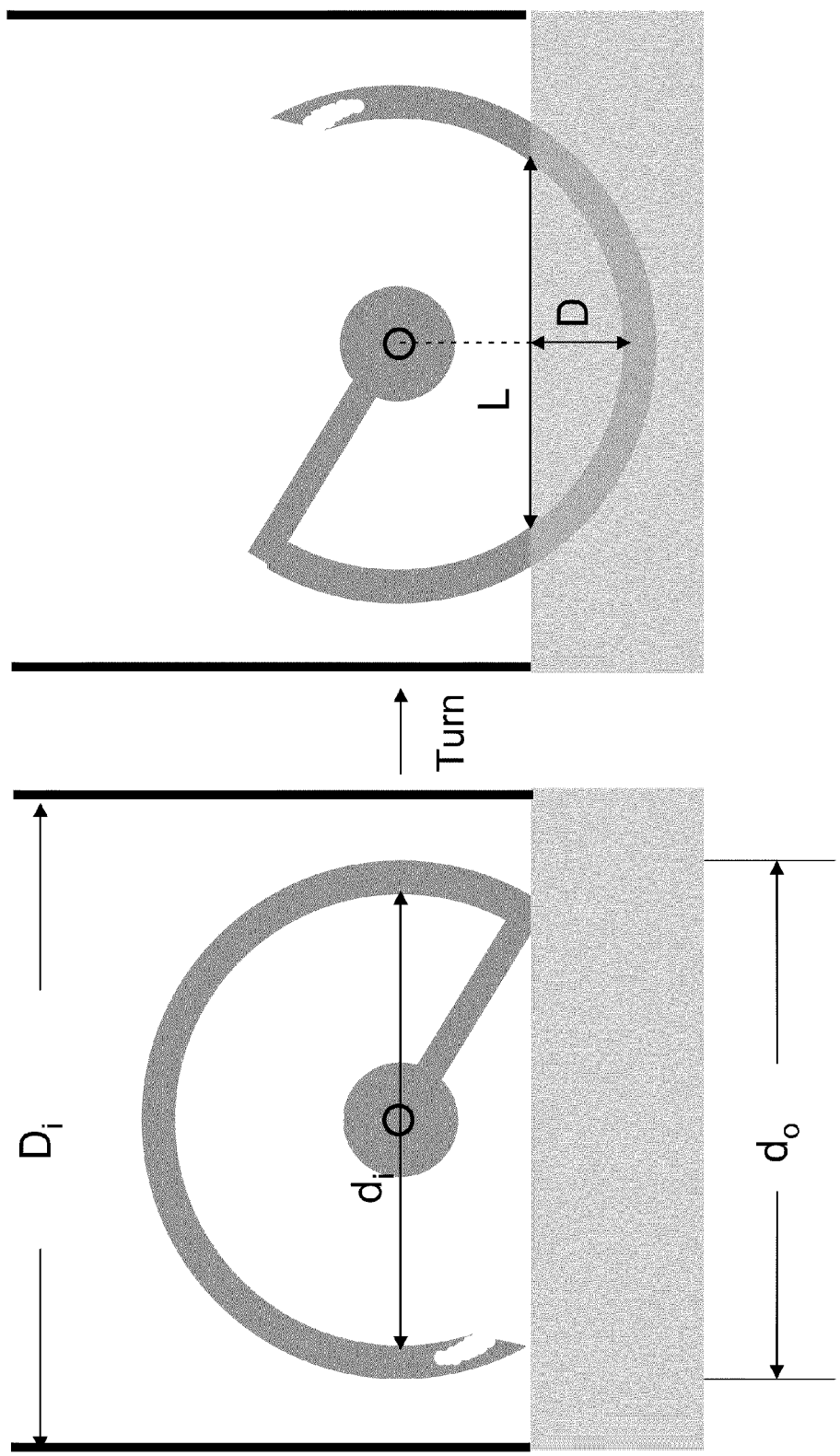
FIG. 4 is a schematic of suture dimensions resulted from use of the curved needle in FIG. 2

The apparatus of this invention can have various sizes, preferably a size suitable for preparing an AF defect. Take the pair of curved needles 140 for example, they each can be configured to have various sizes (e.g., body length, radius, and cross-section diameter of the needle body), depending upon factors such as the inner diameter of the guiding tube, sizes of AF defects (e.g., wound depth, width, and length), and desired results from AF repair. In addition, the distance between the pair of needles 140 can also vary defending on the same factors mentioned above. As illustrated in FIG. 4, needle 140, placed inside a guiding tube 410, has a slightly smaller outer diameter "$d_o$" than the inner diameter of the tube, i.e., "$D_i$." The suture depth "D" and length "L" depend from the inner diameter "$d_i$" and the body length "$l_b$" (or arc length) of needle 140. More specifically, D and L can be calculated by the following equations:

$$D = d_i \times [1 - \cos(\pi - l_b/d_i)]/2$$

$$L = d_i \times \sin(\pi - l_b/d_i)$$

The suture width is equal to the distance between the two needles. The maximum distance between the needles $W_{max}$ is determined by the equation below:

$$W_{max} = D_i \times \cos[\arcsin(d_o/D_i)]$$

Typically, the microdiscectomy wound has dimensions in the millimeter range. Accordingly, it is preferred that the diameter of the needle is less than 10 mm (e.g., 4.5 mm, 4 mm, 3 mm, or 2 mm) and distance between the needles is less than 10 mm (e.g., 5 mm or 3 mm). In some embodiments, suture length is intentionally set to be smaller than the defect length, in which case, two or more MPSS sutures can be placed at about equal distances along the sides of the defect in the anulus, to improve overall suture strength. The cross-section diameter of the needle, i.e., $d_o - d_i$, is preferably not greater than 2 mm (e.g., ranging from 0.4 mm to 2 mm or 0.5 mm to 1 mm).

Figure 5A:
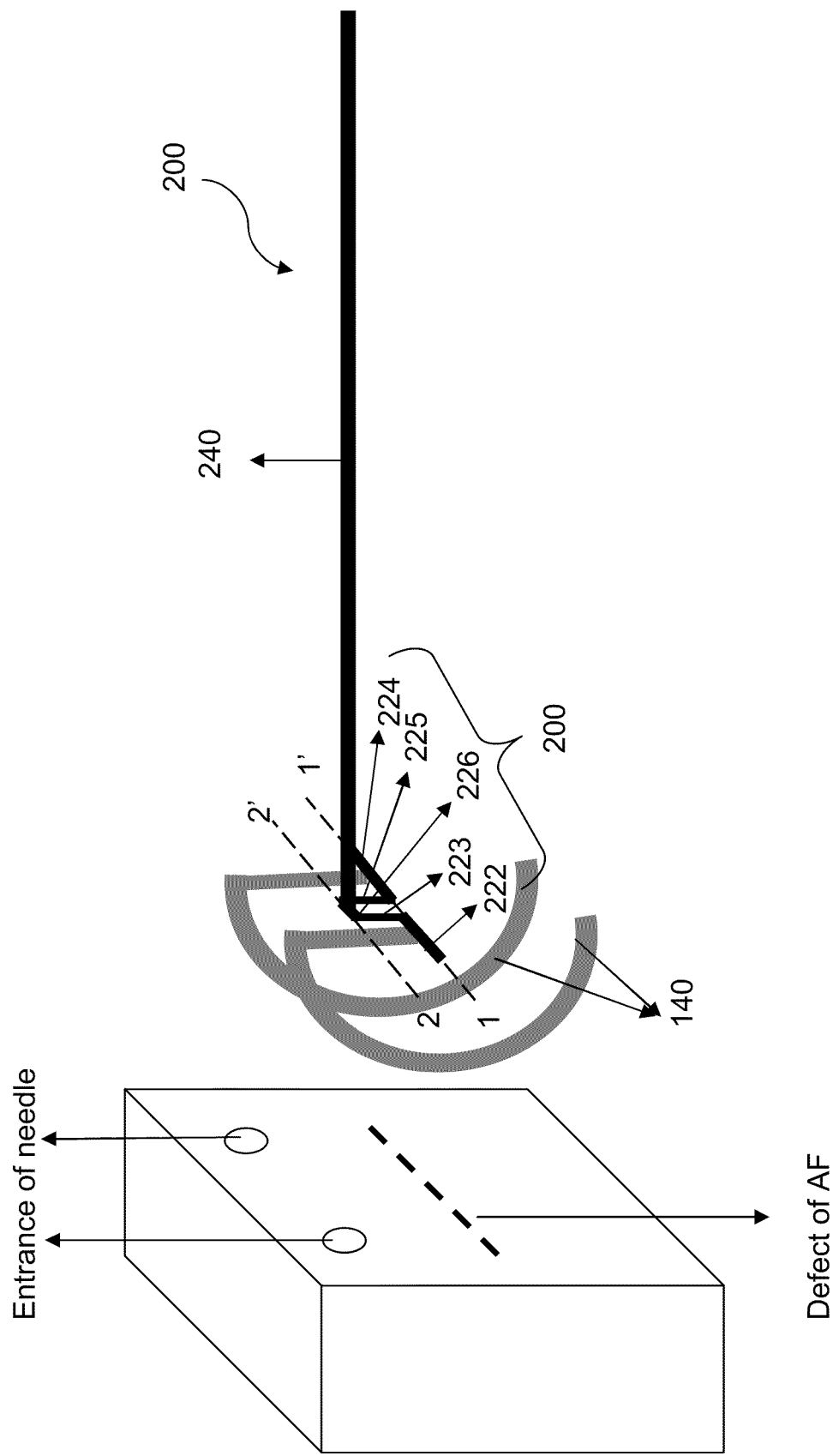

FIGS. 5A-5B illustrate a prototype of a second embodiment of the anulus repair apparatus of this invention.

As shown in FIG. 5A, apparatus 200 includes a pair of curved needles 140 mounted in parallel on a crankshaft 220. Crankshaft 220 consists of a pair of juxtaposed base shafts 222 and 224 whose rotation axes are aligned on line 1-1', a pair of cranks 223 and 225 respectively attached to shafts 222 and 224 at right angles, and a center shaft 226, having a longitudinal axis 2-2' parallel to line 1-1', connected to both cranks 223 and 225. The pair of needles, secured to shafts 222 and 224, can rotate about the rotation axis of the shafts. A pole 240 having one end connected to the center shaft is used to drive the needles to rotate by moving along its longitudinal axis 251. More specifically, cranks 223 and 225 convert the linear movement of the pole to a rotary movement of the needles about line 1-1'.

FIG. 5B illustrates an alternative loop drawing device to that shown in FIGS. 1A-1C. The alternative example includes a hollow pole 250 and a third curved needle 260 mounted on its end rotatable about its rotation axis 251. The hollow pole is coaxially mounted on pole 240 so as to slide along the direction of axis 251. The third needle, when brought approximate to the loops (not shown in this figure) of a suture formed by the method described above, is rotated to seize the loops and then pull them away from needles 140 by rotating and pulling the hollow pole.

Without further elaboration, it is believed that the above description has adequately enabled the present invention. The following examples are, therefore, to be construed as merely illustrative, and not limitative of the remainder of the disclosure in any way whatsoever. All of the publications cited herein are hereby incorporated by reference in their entirety.

Example 1

Evaluation of Suture Tightness

The modified purse-string suture ("MPSS") of this invention was evaluated for its tightness in closing up a cut in a piece of porcine skin, which imitated a surgical wound in the AF. For comparisons, two conventional sutures: simple and cross sutures, were also tested.

Back region skins of experimental mini pigs were collected. Then excessive fat and tissues of the skins were removed to leave the skin tissues. Next, the treated skins were cut into three 20 cm×20 cm pieces with a thickness of 5 mm. Afterward, each of the three porcine skin pieces was tightly fixed onto and covered one end of a cylinder (12.7 cm in diameter and 21 cm in height) with two open ends. A cut (5 mm long, 0.5 cm wide, and 5 mm deep) was created at the center of each skin piece with a sharp scalpel (Feather Inc.). The cuts in three skin pieces were then repaired with MPSS, simple suture, and cross suture, respectively, with a 3-0 non-absorbable monofilament nylon suture.

The tightness of the three sutures was evaluated by measuring the maximum hydrostatic pressure the sutured cuts can sustain. The cylinders were suspended with the covered end facing down. Water was continuously added to the cylinders from the other ends until the repaired cuts started to leak. It was unexpectedly observed that the cut repaired with a cross suture started to leak with 50 mL of water, the cut repaired with a simple suture started to leak with 200 mL of water, while the cut repaired with the MPSS was still leak free with 2600 mL of water. The observation indicates that MPSS sustains much higher pressure (i.e., more than 10 times) than the two conventional sutures do.

Example 2

In Vitro Biomechanical Evaluation of AF Repair (i) Axial Compression

Two defects (both 3.8 mm long, 0.4 mm wide, and 11 mm deep) were created in the left anterior and right anterior regions of a porcine lumbar intervertebral disc respectively. One defect was repaired with the MPSS and the other with a simple suture. Before the compression test, the repaired intervertebral disc was first fixed with epoxy and a blue dye, methylene blue (Sigma M-4159, 2% w/v) mixed with 2.5% w/v alginate gel (Sigma, 250 cps for 2% w/v), was then injected into the NP. The test was done in the manner described in "Intervertebral disc herniation: studies on a porcine model exposed to highly repetitive flexion/extension motion with compressive force," Clin Biomech (Bristol, Avon), 2001, 16(1): 28-37. Measurements were performed using an Instron 4476 from Instron Inc. at a loading rate of 1 mm/min. A preload of 15 N was applied first to detect any leakage.

Unexpectedly, the MPSS repaired defect can sustain up to 2200±30 N compression force while the simple suture repaired defect can sustain 1000±30 N compression force.

(ii) Axial Fatigue

A defect (3.8 mm long, 0.4 mm wide, and 11 mm deep) was created either in the left anterior or right anterior region of a porcine lumbar intervertebral disc. It was then repaired with the MPSS. Before the fatigue test, the repaired intervertebral disc was first fixed with epoxy and a blue dye was then injected into the NP. The test was performed in two sections. In the first section, pre-force interval was set to be between 300-1000 N, frequency was set to be 0.1, 0.2, or 0.5 Hz, and number of cycles was set to be 100 times. Then the frequency was fixed to be 0.2 Hz, force interval was set to be 300-1500 N and number of circles to be 500 times, and force interval was set to be 500-2000 N and number of circles to be 300 times. In the second section, the pre-force interval was set to be 100-300 N, pre-cycles to be 360 times, frequency to be 5 HZ, force interval to be 100-500 and 100-10000 N, number of circles 1000 times.

It was unexpectedly observed that when the pre-force interval was set to be between 300-1000 N and number of cycles was set to be 100 times, NP did not leak when frequency was increased from 0.1 to 0.2 and lastly to 0.5 Hz. Neither did NP leak under the other conditions of the first section or conditions of the second section.

Example 3

In Vivo Evaluation of AF Repair and Molecular Biology Analysis

A total of 6 four-month old male mini pigs (30-40 kg) were used in the study. The pigs were fasted 24 hours before surgery. 2% isoflurane was used as an anesthetic. All surgeries were performed using aseptic techniques. In the surgery, a wound 4 mm×11 mm) was created in a cervical intervertebral disc (C3/4-C5/6). The wound was sutured with MPSS. For comparisons, the wound was either not repaired or repaired with a simple suture. The intact C1/2 intervertebral disc was evaluated as blank control.

The pigs were examined with X-ray and MRI 2, 4, and 6 months post surgery before the intervertebral discs were collected. The X-ray and MRI results showed that unrepaired intervertebral discs exhibited obvious degeneration while the repaired discs did not.

The nucleus pulposus (NP) was extracted from each of the collected discs (including MPSS repaired, simple suture repaired, and blank control). Total RNA was then isolated from each of the NP samples. Nest, the total RNA was subject to reverse transcription to produce cDNAs. Quantitative Real-Time PCR ("qRT-PCR") was then performed using Roche Applied System to detect levels of mRNAs of the target genes, i.e., extracellular matrix gene (e.g., collagen type I or II, aggrecan) and inflammatory mediator gene (e.g., MMP-13). Unexpectedly, at month 6, the repaired group showed an increased level of expressions of collagen type II and aggrecan and a decreased level of expression of collagen type I and MMP-13, compared to unrepaired group, and showed similar level of expressions of extracellular matrix gene and MMP-13 compared to intact NP. The results suggest that AF repair at least decelerated the degree of degeneration compared to non-repaired AF.

Example 4

In Vivo Evaluation of AF Repair and Biomechanical Analysis

A total of 3 four-month old male mini pigs (30-40 kg) were used in the study. The pigs were fasted 24 hours before surgery. 2% isoflurane was used as an anesthetic. All surgeries were performed using aseptic techniques. In the surgery, a wound (4 mm×11 mm) was created in each of the four lumbar intervertebral discs (L1/2-L4/5). The L1/2 wound was not repaired, the L2/3 wound was sutured with MPSS, the L3/4 wound was repaired with a simple suture, and the L4/5 wound was sutured with a cross suture.

The intervertebral discs were collected 4 weeks post surgery and evaluated using discomanometry. The test was conducted in a manner similar to that described in Schechtman et al., "Failure strength of the bovine caudal disc under internal hydrostatic pressure," J Biomech 2006, 39: 1401-9. In brief, the intervertebral discs were cleaned by removing all surrounding soft tissues. The cleaned discs were then hydrated in 0.15M saline to ensure that all of them were in the same hydrated state before the test. A blue dye, methylene blue (Sigma M-4159, 2% w/v) mixed with 2.5% w/v alginate gel (Sigma, 250 cps for 2% w/v), was then injected into the fully hydrated NP via an axial root through an attached vertebra, thus eliminating any damage to the AF. All of the injected discs were pressurized using an MTS machine, Instron 4476 (Instron Inc.) to the point where all 3 indicators of disc failure (i.e., a sharp pressure vs. time discontinuity, audible fibrous tearing, and sudden gel coloration of the outer anulus) were observed simultaneously. Measurements were performed using a loading rate of 5 mm/min. No preload was applied at first.

The test results indicated that the MPSS-repaired defect was tighter and stronger than the unrepaired defect and defects repaired by the other two sutures. As such, the MPSS suture provided a better preservation of the NP.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. For example, the repair apparatus may have only one curved needle mounted on the shaft or more than two curved needles that are mounted in parallel on the shaft. In the case of one curved needle, a mechanism for moving the needle along the shaft may be integrated in the apparatus to allow the needle to form multiple loops of a suture passing through the concavity of the needle. When the apparatus contains more than two curved needles, a suture similar to MPSS can be formed. The apparatus can be used to repair other tissues or organs.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A suturing apparatus comprising:

a shaft;

a pair of curved suturing needles, each needle including a substantially semi-annular body having a proximal end, a distal end, a tip at the distal end, an inner periphery, and an outer periphery, and an arm extending radially inward from the proximal end, in which a concavity, having a permanent opening that faces the distal end, is formed in the body proximate to the distal end, the concavity extending from the permanent opening only in a direction away from the tip, the pair of needles being mounted in parallel on the shaft such that the shaft extends through an end of the arm of each needle opposed to the proximal end and in a direction transverse to a plane formed by the body and the arm; and a rotational driving mechanism connected to the shaft, wherein a longitudinal axis of the shaft corresponds to a rotation axis thereof, the pair of needles each have a co-center of the inner and outer peripheries, both co-centers being on the rotation axis, and the rotational driving mechanism, configured to rotate the shaft and the pair of needles about the rotation axis, includes a gear system and a bar, in which the gear system has a first gear coaxially connected to the shaft and a second gear that is perpendicularly engaged with the first gear and coaxially connected to the bar.

2. The apparatus of claim 1, wherein the concavity is formed at the distal end of the body.

3. The apparatus of claim 1, wherein the rotational driving mechanism is a device for transmitting a first rotary motion to a second rotary motion.

4. The apparatus of claim 1, further comprising a tube member configured to support and partially house the bar, wherein the tube member has a first open end, a second open end opposed to the first end, and a longitudinal axis parallel to a longitudinal axis of the bar.

5. The apparatus of claim 4, further comprising a loop drawing device including a pair of hooks mounted in parallel on an end of a second bar perpendicular to the shaft, wherein each of the pair of hooks is aligned opposed to each of the pair of needles for seizing a loop of a suture passing through the concavity of each needle, and the second bar is supported and partially housed by the tube member.

* * * * *